United States Patent [19]

Soelkner

[11] Patent Number: 5,042,302
[45] Date of Patent: Aug. 27, 1991

[54] PHASE-ACCURATE IMAGING AND MEASURING OF ELASTIC WAVE FIELDS WITH A LASER PROBE

[75] Inventor: Gerald Soelkner, Ottobrunn, Fed. Rep. of Germany

[73] Assignee: Siemens Aktiengesellschaft, Munich

[21] Appl. No.: 500,916

[22] Filed: Mar. 29, 1990

[30] Foreign Application Priority Data

May 12, 1989 [EP] European Pat. Off. ......... 89108609.2

[51] Int. Cl.$^5$ ............................................. G01N 29/06
[52] U.S. Cl. ........................................ 73/597; 73/643; 356/372
[58] Field of Search ................. 73/643, 653, 655, 657, 73/597 I; 356/432 T, 372

[56] References Cited

U.S. PATENT DOCUMENTS

| | | | |
|---|---|---|---|
| 4,652,744 | 3/1987 | Bowers et al. | 73/657 |
| 4,659,224 | 4/1987 | Monchalin | 73/657 |
| 4,928,527 | 5/1990 | Burger et al. | 73/657 |

Primary Examiner—Hezron E. Williams
Assistant Examiner—Rose M. Finley
Attorney, Agent, or Firm—Hill, Van Santen, Steadman & Simpson

[57] ABSTRACT

Heretofore, models for calculating the wave propagation in SAW components did not consider all physical effects, deviations between realized and desired component behavior therefore frequently occur. In order to improve such models, the wave field in the component is imaged in a phase-accurate manner or to measure the parameters that characterize the elastic wave in a topically-resolved manner. Herein, the deflection of the component surface produced by the elastic wave is quantatively acquired by measuring the deflection of a pulsed laser beam. A mode-coupled Nd:YAG laser with a subsequent pulse compressor is used as the radiation source.

13 Claims, 1 Drawing Sheet

PHASE-ACCURATE IMAGING AND MEASURING OF ELASTIC WAVE FIELDS WITH A LASER PROBE

BACKGROUND OF THE INVENTION

1. Field of the Invention

The present invention relates to a method for phaseaccurate imaging and measuring of elastic wave fields with a laser probe in which elastic waves are excited on a specimen, in which a laser beam is directed onto the specimen surface, in which the deflection of the reflected laser beam caused by an undulation of the specimen surface is detected, and in which a measured signal proportional to the undulation is generated. Apparatus for implementing the method is provided along with an optical system for focusing the laser beam onto the specimen surface. A radiation detector documents the deflection of the reflected laser beam produced by the undulation of the specimen surface, and a device generates a measured signal proportional to the undulation.

2. Description of the Prior Art

Components in which elastic waves, particularly acoustic surface waves, are excited by transducer structures on piezoelectric materials and are detected are acquiring increasing significance in communications and high-frequency technology. Since planar technology allows an extremely accurate and economical manufacture of these systems, the same have been optimized with the assistance of the methods of computer-aided design (CAD). Since the models employed for the calculation of the wave propagation do not consider all physical effects (reflections at edges, diffraction phenomena, etc), deviations between realized and desired component behavior frequently occur. For improving the CAD models, it is therefore necessary to image the wave field in the component with accurate phase or, respectively, to measure the parameters that characterize the elastic wave (amplitude, phase, propagation speed) topically resolved.

IEEE Transactions on Sonics and Ultrasonics, Vol. SU-25, No. 6, 1978, pp. 372-377, describes a method for imaging acoustic surface wave fields in which the Surface Acoustic Wave (SAW) component is scanned point-by-point with an intensity-modulated laser beam. The imaging of a large wave field is extremely time consuming since the acquisition of the measured value requires a few seconds at each of the respective scan locations.

SUMMARY OF THE INVENTION

The object of the present invention is to provide a method of the type generally set forth above with which extensive wave fields can be phase-accurately imaged and measured in considerably shorter time. An attendant object is to provide apparatus for implementing the method in which the apparatus should have a great bandwidth.

The above object is achieved, according to the present invention, in a method for phase-accurate imaging and measuring of elastic wave fields with a laser probe wherein elastic waves are cited on a specimen, a laser beam is directed onto the specimen surface, the deflection of the reflected laser beam caused by an undulation of the specimen surface is detected, and the measured signal proportional to the undulation is generated, and is particularly characterized in that a pulsed laser beam is employed whose pulse repetition rate $f_{LA}$ is lower than the frequency $f_{SAW}$ of the elastic waves, in that a reference signal having the frequency $f_R = |f_{SAW} - nf_{LA}|$ is generated, where n references a natural number, and in that the amplitude of the measured signal is determined in a phase-sensitive manner upon utilization of the reference signal and is registered.

The attendant object is achieved, according to the invention, in apparatus for the phase-accurate imaging and measuring of elastic wave fields for practicing the above method, in which the apparatus comprises a laser probe, a device for generating elastic waves on a specimen, a laser beam source, an optical system for focusing the laser beam onto the specimen surface, a first radiation detector for the documentation of the deflection of the reflected laser beam produced by the undulation of the specimen surface, and a device for generating a measured signal proportional to the undulation, and is particularly characterized by an optical pulse generator whose pulse repetition rate ($f_{LA}$) is lower than the frequency ($f_{SAW}$) of a first signal that drives the device for generating the elastic waves, by a phase-sensitive detector including a first input which is charged with the measured signal, by a mixer including an output connected to a reference input of the phase-sensitive detector, the mixer including a first input which is charged with the first signal and a second input charged with a second signal, whereby the frequency of the second signal corresponds to the pulse repetition rate ($f_{LA}$) of the optical pulse generator.

The advantage to be obtained in practicing the present invention is, in particular, that extensive wave fields can also be imaged and measured in a short time. Moreover, the present invention allows measurements at SAW components that work at frequencies above 5-10 GHz.

BRIEF DESCRIPTION OF THE DRAWING

Other objects, features and advantages of the invention, its organization, construction and operation will be best understood from the following detailed description, taken in conjunction with the accompanying drawings, on which.

DESCRIPTION OF THE PREFERRED EMBODIMENTS

Figure 1:
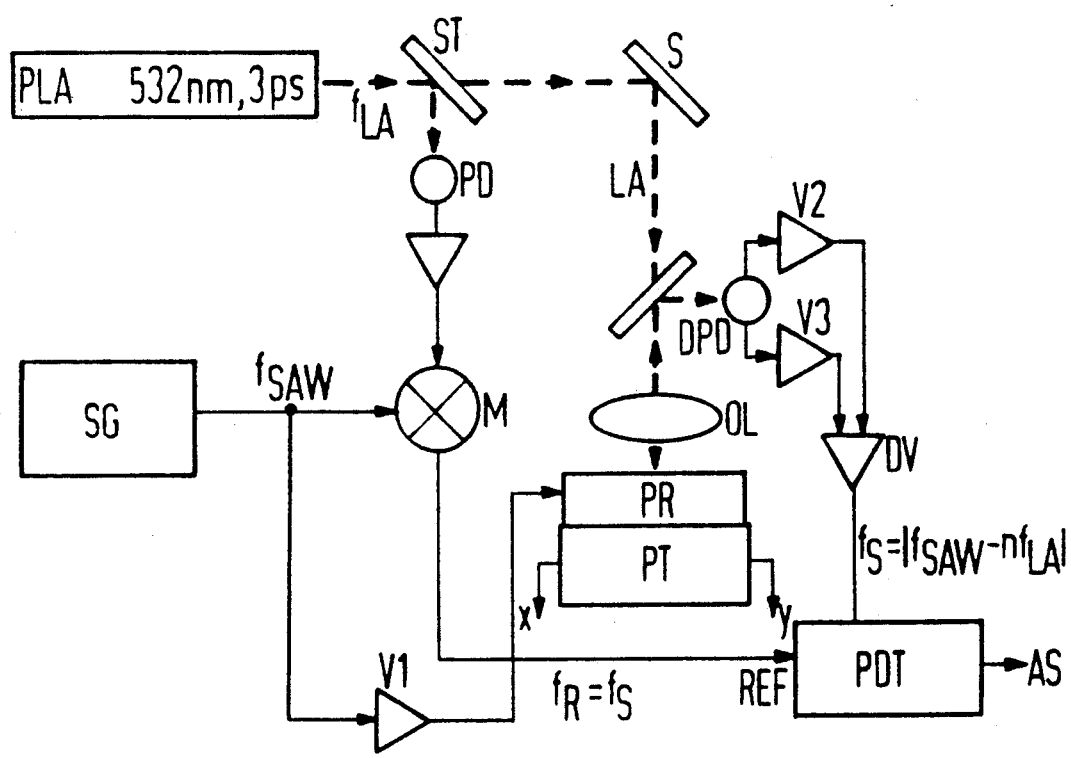
FIG. 1 is a schematic representation of an exemplary embodiment of an apparatus for implementing the method of the present invention.

Referring to FIG. 1, apparatus for phase-accurate measurement of the amplitude of acoustic surface waves in an SAW component PR (For example, IF filter, convolver or pulse compressor) is schematically illustrated. The component PR is arranged on a positioning table PT, the interdigital transducers of the SAW component PR are driven by a signal generator SG by way of an interposed amplifier V1. The alternating voltage having the frequency $f_{SAW}$ applied to the electrodes of the transducer leads by way of the piezoelectric effect to a periodic deformation of the crystal surface, the periodic deformation propagating across the component PR as an acoustic wave having a velocity of approximately 300-400 m/s. This wave, whose frequency corresponds to the frequency $f_{SAW}$ of the signal that drives the transducer, penetrates into the crystal to a depth $d \approx \lambda_{SAW}$ ($\lambda_{SAW}$ = wavelength of the acoustic surface wave), whereby the amplitude of the surface oscillation can amount to approximately 0.1–10 Å. A pulsed laser beam LA is used for documentation of the deformation of the surface produced by the elastic wave, the laser beam LA being generated in an optical pulse generator PLA, deflected at a mirror S and focused onto the component PR with the assistance of a lens system OL. The magnification of the lens system OL is thereby prescribed such that the beam diameter d on the crystal satisfies the condition $$d < \lambda_{SAW}.$$

The optical pulse generator PLA is preferably composed of a mode-coupled Nd:YAG laser (Spectra-Physics, Model 3000: $\lambda = 1064$ nm, pulse width, $T_p = 80$ ps pulse repetition rate $f_{LA} = 82$ MHZ), a pulse compressor (Spectra-Physics, Model 3600) for reducing the width of the Nd:YAG laser pulses to $T_p < 5$ ps, and a frequency doubling KTP crystal that halves the wavelength of the laser emission to $\lambda = 532$ nm. The utilization of this picosecond laser source (pulse power: $W \approx 2$ kw, mean power: $\overline{W} \approx 500$ mW) guarantees a high chronological resolution, whereby the time structure of the laser pulses ($T_{92} \approx 3$ ps) lends the measuring method a bandwidth for the following $> 10$ GHz needed for the investigation of SAW components.

The angular deflection of the reflected laser beam caused by the mechanical undulation of the specimen surface is detected with the assistance of a detector PDT composed of two photodiodes and two amplifiers V2, V3 whose output signals are applied to the inputs of the differential amplifier DV. Since the pulse repetition rate $f_{LA}$ of the laser source PLA is lower than the frequency $f_{SAW}$ of the acoustic surface waves, the output signal of the differential amplifier DV supplied to the input of a phase-sensitive detector PDT has a frequency $f_S$ that is calculated $$f_S = |f_{SAW} - nf_{LA}|$$

(n = natural number). A lock-in amplifier at whose output a signal AS proportional to the excursion of the crystal surface appears particularly comes into consideration as a phasesensitive detector PDT. The signal AS is recorded, dependent on location, whereby the location information, i.e. the coordinates of the respective measuring point within the component PR, is taken at the corresponding outputs x, y of the positioning table PT. When, for example, a deflection unit composed of two rotatable galvanometer mirrors is available for positioning the laser beam LA, the output signals of a scan generator that controls the deflection unit, the output signals defining the location of the measuring point, of course, can also be recorded.

The reference signal REF supplied to the phase sensitive detector PDT is generated in a mixer M that has its input connected to receive the amplified output signal of a photodiode PD and to receive the output signal of the signal generator SG that drives the component PR. Since the intensity of the laser beam (which is generated with the assistance of a beam splitter ST) incident on the photodiode PD changes with the pulse repetition rate $f_{LA}$ generated by the laser source PLA, the mixer M generates a reference signal REF whose frequency $f_R$ corresponds to the frequency $f_S$ of the output signal of the differential amplifier DV. Both signals have a chronologically-constant phase shift for the respective measuring point whose amount is dependent o the location of the measuring point within the component PR.

Figure 2:
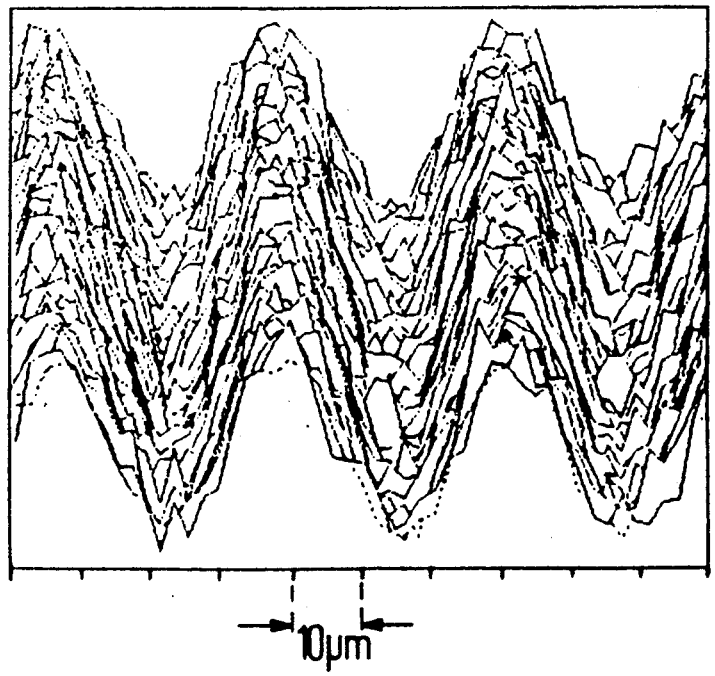
FIG. 2 is a graphic illustration of an acoustic wave field in an OFW bandpass filter.

An image of the acoustic wave field acquired with apparatus constructed in accordance with the present invention in an SAW band-pass filter driven with sine voltage having the frequency $f_{SAW} = 110$ MHz is schematically illustrated in FIG. 2. The measuring time for recording this image constructed of $50 \times 50$ scan points (scan field: 100 µm $\times$ 100 µm, x/y step distance: 2 µm integration time per scan point: 50 m/s) amounted to about 120 seconds. However, it can also be considerably reduced when the positional change is not undertaken by a mechanical displacement of the component PR, but by fast deflection of the laser beam LA. Since, as a consequence of the high signal-to-noise ratio, the acquisition of a measured value respectively requires only a few ms (in the known method, the average dwell time of the laser beam on a measuring point amounts to about 8 seconds), the practice of the present invention particularly allows the employment of fast deflection systems utilized in scanning laser microscopes.

The present invention is not limited to the described exemplary embodiments. Therefore, it is possible without further measures to replace the lock-in amplifier with a sample-and-hold circuit. An edge-triggered monoflop at whose input the reference signal REF generated by the mixer M is applied is preferably employed for driving the gate. The phase-sensitive detector PDT can, in particular, be realized in the form of a boxcar unit.

Although I have described my invention by reference to particular illustrative embodiments thereof, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim:

1. Apparatus for phase-accurate imaging and measuring of elastic wave fields on a specimen, comprising:

signal generator means operable to produce a first signal having a predetermined frequency $f_{SAW}$ said signal generator means connected to the specimen for driving the specimen to produce elastic waves on a surface thereof;

optical pulse generating means operable to generate a pulsed light beam having a pulse repetition rate $f_{LA}$ that is lower than the frequency $f_{SAW}$ of the first signal;

beam splitting means for dividing the light beam into first and second light beams;

optical detector means for receiving the first light beam and responsive thereto to produce a second signal having the frequency $f_{LA}$ of the pulse repetition frequency of the pulsed light beam;

mixer means connected to said signal generator means and to said optical detector means for producing a reference signal having a frequency $f_R = |f_{SAW} - nf_{LA}|$, where n is a natural number;

a radiation detector;

beam focusing means for receiving and focusing said second light beam onto the surface of the specimen, the undulations of the elastic wave effecting corresponding reflections as a reflected light beam reflected back to said beam focusing means, said beam focusing means including beam directing means for directing the reflected beam to said radiation detector;

said radiation detector operable in response to the reflected beam to produce a third signal having a frequency $f_s = |f_{SAW} - nf_{LA}|$; and phase-sensitive detector means connected to said mixer means and to said radiation detector means for producing an output signal whose amplitude is dependent on the phase of the third signal with respect to the reference signal.

2. The apparatus of claim 12, wherein said optical pulse generating means comprises:
a picosecond pulsed laser source.

3. The apparatus of claim 2, wherein said laser source comprises:
a mode-coupled Nd: YAG laser generator.

4. The apparatus of claim 2, wherein said laser source comprises:
a mode-coupled nd: YAG laser generator producing an output having a wave length of 1064 nm, a pulse width of 80 ps and a pulse repetition rate of 82 MHz;
a pulse compressor for reducing the pulse width to less than 5 ps; and
a frequency doubler for reducing the wave length of the laser emission to 532 nm.

5. The apparatus of claim 1, wherein said signal generator means comprises:
a signal generator; and
an amplifier connected between said signal generator and the specimen.

6. The apparatus of claim 1, wherein said beam splitting means comprises:
a beam splitting mirror which deflects light of the light beam as the first light beam and passes light of the light beam as the second light beam.

7. The apparatus of claim 1, wherein said radiation detector comprises:
first and second photodiodes; and
a differential amplifier connected to said first and second photodiodes.

8. The apparatus of claim 7, and further comprising:
first and second amplifiers respectively connected between said first and second photo diodes and said differential amplifier.

9. The apparatus of claim 1, wherein said beam focusing means comprises:
a pair of galvanometer mirrors for directing said second beam towards the specimen; and
a lens system interposed between said pair of galvanometer mirrors and the specimen.

10. The apparatus of claim 1, wherein said optical detector means comprises:
a photo diode; and
an amplifier connected between said photo diode and said mixer means.

11. A method for phase-accurate imaging and measuring of elastic wave fields comprising the steps of:
exciting elastic waves on the surface of a specimen having a frequency of $f_{SAW}$ causing surface undulations;
generating and directing a pulsed laser beam having a pulse repetition frequency $f_{LA}$ onto the surface of the specimen, the pulse repetition frequency $f_{LA}$ being lower then the frequency $f_{SAW}$ of the elastic waves, the laser beam being reflected from the specimen surface and deflected by the surface undulations caused by the elastic waves;
receiving the reflected laser beam and generating a measured signal therefrom representing the undulations;
generating a reference signal having a frequency $f_R$ in a accordance with the expression $f_R = |f_{SAW} - nf_{LA}|$, where n is a natural number; and
utilizing the reference signal as a phase reference to determine the amplitude of the measured signal.

12. An apparatus for phase-accurate imaging of elastic wave fields on a specimen comprising:
a drive device for exciting elastic waves on a surface of the specimen, the elastic waves having a frequency $f_{SAW}$;
means for generating a pulsed laser beam whose pulse repetition frequency $f_{LA}$ is lower than the frequency $f_{SAW}$ of the elastic waves;
means for focusing the laser beam onto the specimen surface;
a first detector unit for the documentation of the laser beam reflected from the specimen surface and deflected by the undulations of the specimen surface;
means for generating a measured signal representing the undulations of the specimen surface in response to the reflected and detected laser beam;
means for generating a reference signal having the frequency $f_R = |f_{SAW} - nf_{LA}|$, where n is a natural number; and
a phase-sensitive detector connected to said means for generating a reference signal and to said first detector unit for producing a phase-defined signal representing the amplitude of the measured signals.

13. The improved apparatus of claim 12, wherein: said means for generating the reference signal comprises a beam splitter producing a further laser beam, a second detector unit, including a phase-sensitive detector, for receiving the further laser beam, and a mixer connected to said second detector unit and to said drive means.

* * * * *